US012697443B2

(12) United States Patent
Cai

(10) Patent No.: US 12,697,443 B2
(45) Date of Patent: Aug. 4, 2026

(54) AIR DETECTION METHOD FOR PUMPS WITH VOLUME MEASUREMENT

(71) Applicant: CareFusion 303, Inc., San Diego, CA (US)

(72) Inventor: Frank Cai, Ontario, CA (US)

(73) Assignee: CAREFUSION 303, INC., San Diego, CA (US)

( * ) Notice: Subject to any disclaimer, the term of this patent is extended or adjusted under 35 U.S.C. 154(b) by 312 days.

(21) Appl. No.: 18/195,318

(22) Filed: May 9, 2023

(65) Prior Publication Data

US 2024/0374844 A1     Nov. 14, 2024

(51) Int. Cl.
*A61M 5/36*          (2006.01)
*A61M 5/142*          (2006.01)
*G01L 1/16*          (2006.01)

(52) U.S. Cl.
CPC ........ *A61M 5/365* (2013.01); *A61M 5/14228* (2013.01); *G01L 1/16* (2013.01); *A61M 2205/3327* (2013.01)

(58) Field of Classification Search
CPC .................................................... A61M 5/365
USPC .......................................................... 73/168
See application file for complete search history.

(56) References Cited

U.S. PATENT DOCUMENTS

| | | | | | |
|---|---|---|---|---|---|
| 6,142,008 | A | * | 11/2000 | Cole | G01N 29/02 |
| | | | | | 604/122 |
| 7,547,295 | B2 | * | 6/2009 | Cassidy | A61M 5/16813 |
| | | | | | 604/122 |
| 2017/0028140 | A1 | | 2/2017 | Toshima | |
| 2017/0143898 | A1 | | 5/2017 | Grosse-Wentrup et al. | |
| 2019/0298913 | A1 | * | 10/2019 | Biasi | A61M 5/44 |
| 2022/0233763 | A1 | | 7/2022 | Zhang et al. | |
| 2022/0235755 | A1 | | 7/2022 | Cai et al. | |
| 2022/0401640 | A1 | * | 12/2022 | Jacobson | G16H 40/40 |

OTHER PUBLICATIONS

International Search Report and Written Opinion for Application No. PCT/US2024/027630, dated Aug. 6, 2024, 11 pages.

* cited by examiner

Primary Examiner — Walter L Lindsay, Jr.
Assistant Examiner — Philip T Fadul
(74) Attorney, Agent, or Firm — MASCHOFF BRENNAN

(57) ABSTRACT

Methods of air detection in pumps are described herein. In certain embodiments, a pump for detecting air includes a plunger, a plunger air detection module, a camshaft, and a first biasing member. The plunger is movable to selectively engage a tubing segment with a fluid. The plunger air detection module is disposed within the plunger. The camshaft is configured to move the plunger between an engaged position in contact with the tubing segment and a disengaged position spaced apart from the tubing segment. The first biasing member is configured to urge the plunger toward the tubing segment to maintain contact with the tubing segment in the engaged position.

20 Claims, 6 Drawing Sheets

AIR DETECTION METHOD FOR PUMPS WITH VOLUME MEASUREMENT

FIELD OF THE INVENTION

The present disclosure generally relates to methods of air detection in pumps, and, in particular, to methods of air detection in peristaltic pumps.

BACKGROUND

Patients in hospitals often receive medications and medical fluids (e.g., a saline solution or a liquid medication) via infusion using an intravenous ("IV") pump. In some applications, an IV pump uses peristaltic manipulation of a segment of tubing of an IV set to create the flow of medical fluid to the patient. In some applications, volume measurements can be taken and used to detect the rate of fluid flow through the pump.

Rate accuracy can be critical to clinicians and patients in infusion therapy in particular. New technology is being developed to feed the pump control unit information on infusion rate in real time. However, existing methods that are used to measure infusion rate often assume that there is no air in the sub-system that takes the measurement. This is not necessarily a good assumption because the presence of air bubbles in a set is a common occurrence. When air bubbles enter the volume measurement sub-system within the pump, the measurements can become inaccurate. This causes the pump control to erroneously adjust the flow rate, which puts patients in danger of over-infusion, under-infusion, air embolism if the bag runs dry, or blood clots if the bag runs dry and a keep-vein-open (KVO) mode is not initiated, for example.

SUMMARY

The disclosed subject matter relates to peristaltic pumps capable of detecting the presence of air in a tubing segment extending therethrough. In certain embodiment, a pump for detecting air includes a plunger movable to selectively engage a tubing segment comprising a fluid; a camshaft configured to move the plunger between an engaged position in contact with the tubing segment and a disengaged position spaced apart from the tubing segment; and a first biasing member configured to urge the plunger toward the tubing segment to maintain contact with the tubing segment in the engaged position, wherein the plunger comprises a plunger air detection module.

In certain embodiments, the pump includes a backer configured to engage the tubing segment in the engaged position and the disengaged position. The backer includes a channel configured to prevent movement of the tubing segment relative to the pump, wherein the channel extends a longitudinal length of the backer. In certain embodiments, the channel is defined by a front wedge and a rear barrier extending therefrom along a longitudinal length of the backer, and wherein the backer comprises a cutout extending along a longitudinal length thereof. In certain embodiments, the cutout is configured to receive a backer air detection module. In certain embodiments, the backer air detection module is parallel to the plunger air detection module, the plunger air detection module is configured to transmit a signal and the backer air detection module is configured to receive the signal when the plunger is in the engaged position.

In certain embodiments, the plunger air detection module includes a plurality of elements, wherein the plunger air detection module comprises a piezoelectric array of elements. In certain embodiments, the pump includes a slot defined in the plunger, wherein the plunger air detection module is disposed in the slot. In certain embodiments, the plunger does not deform the tubing segment in the engaged position.

In certain embodiments, a method is disclosed and comprises providing a tubing segment within a pump, the tubing segment comprising a fluid traveling therethrough; urging a plunger toward the tubing segment to maintain contact with the tubing segment as the fluid travels therethrough; and emitting a signal from a plunger air detection module of the plunger through the tubing segment. In certain embodiments, the method includes receiving the signal with a backer air detection module of a backer. In certain embodiments, the method includes moving the plunger with a camshaft to increase or decrease the cross section of the tubing segment to modulate the flow of fluid through the tubing segment. In certain embodiments, the method includes moving the plunger with a camshaft to reduce the cross section to prevent the flow of fluid through the tubing segment. In certain embodiments, the backer air detection module is parallel to the plunger air detection module when the plunger is urged toward the tubing segment to maintain contact with the tubing segment. In certain embodiments, the plunger does not deform the tubing segment when the plunger is urged toward the tubing segment to maintain contact with the tubing segment.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to administration of medical fluid by utilizing the disclosed peristaltic pumps, it is to be understood that this description is only an example of usage and does not limit the scope of the claims. Various aspects of the disclosed peristaltic pumps may be used in any application where it is desirable to administer the flow of fluid.

Figure 1:
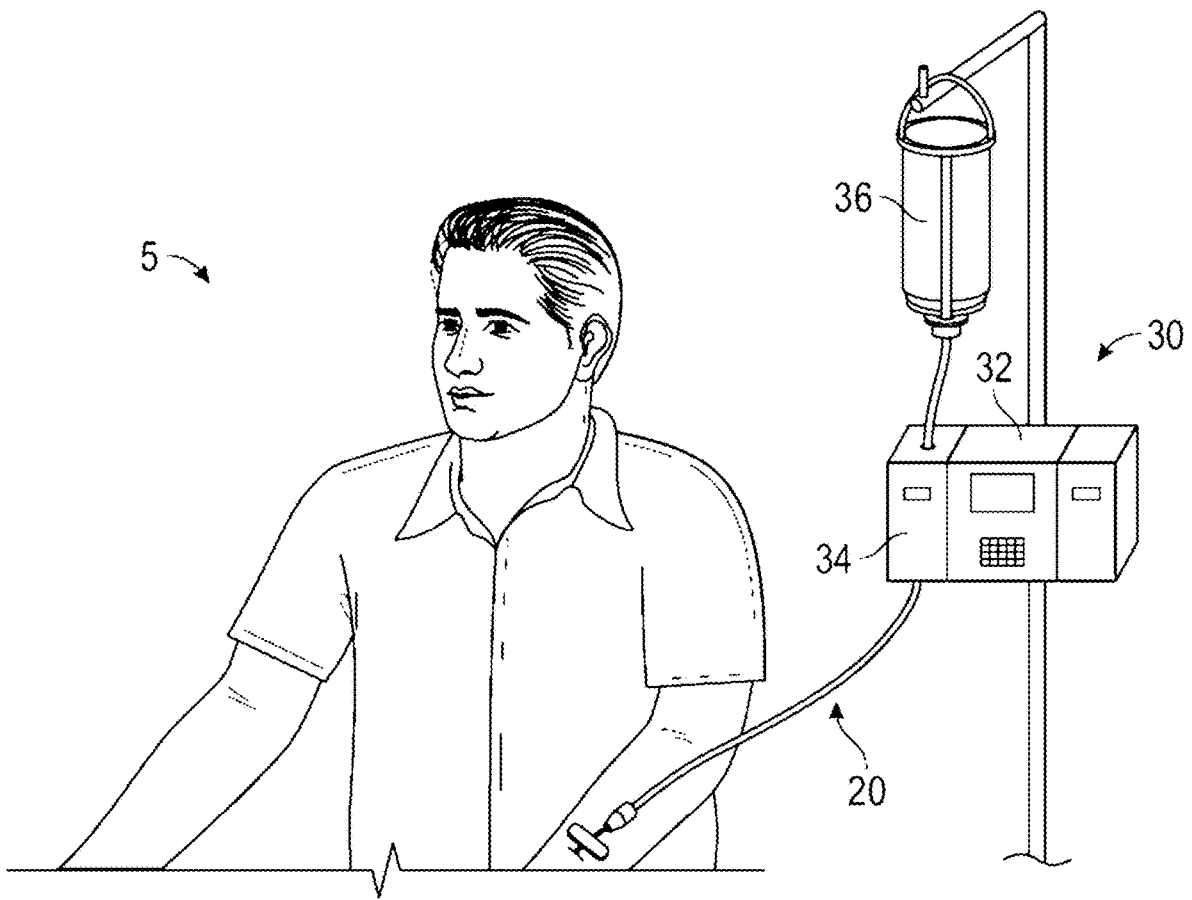
FIG. 1 depicts a patient receiving an infusion of a medical fluid using an IV pump.

FIG. 1 depicts a patient 5 receiving an infusion of a medical fluid using an IV pump 30. In the depicted example, the IV pump 30 is delivering a medical fluid from a fluid container 36 to the patient 5. A fluid container 36 is hung at or above the patient's head and connected via an IV set 20 to the IV pump module 34 and then to the patient 5. In some embodiments, the IV pump 30 includes a control unit 32 and a pumping module 34. Suitable IV pump configurations and systems are described, for example, in U.S. patent application Ser. No. 17/586,619, the entire disclosure of which is hereby incorporated by reference.

The pumping module 34 can include a peristaltic pump to administer the medical fluid from the fluid container 36 to the patient 5. During operation of the peristaltic pump, it may be desirable to monitor the volume pumped by the peristaltic pump. In some applications, the peristaltic pump can include a measurement phase between a refill phase and a delivery phase.

The disclosed peristaltic pump can incorporate various measurement mechanisms to allow for monitoring the volume pumped by the peristaltic pump, as well as the detection of the presence of air. The disclosed peristaltic pump can include feeler mechanisms, biasing members with various levels of force, and/or split plungers. By utilizing the measurement mechanisms disclosed herein, the peristaltic pump can allow for monitoring without a dedicated measurement phase and/or without generating high internal pressures.

The disclosed peristaltic pump overcomes several challenges discovered with respect to certain air detection approaches utilized with IV sets. One challenge with certain air detection approaches is active fluid volume adjustment as a result of air detection. Accordingly, simply adding an in-line air sensor is not sufficient. Air in line sensors may only trigger an alarm or notification to a patient or clinician if an amount of air passing by is above a threshold. Further, air in line sensors assume that all bubbles are traveling downstream. However, in practice bubbles may get stuck or even flow back upwards and trigger the sensor multiple times. Because the fluid volume traveling through the disclosed peristaltic pump may be traveling downstream and the fluid volume is being measured, it is advantageous to provide air in line sensing capabilities to the fluid volume measurement systems to directly measure the amount of air and adjust the measured volume accordingly.

Examples of peristaltic pumps that allow for measurement of a fluid volume and air in line detection are now described.

Figure 2A:
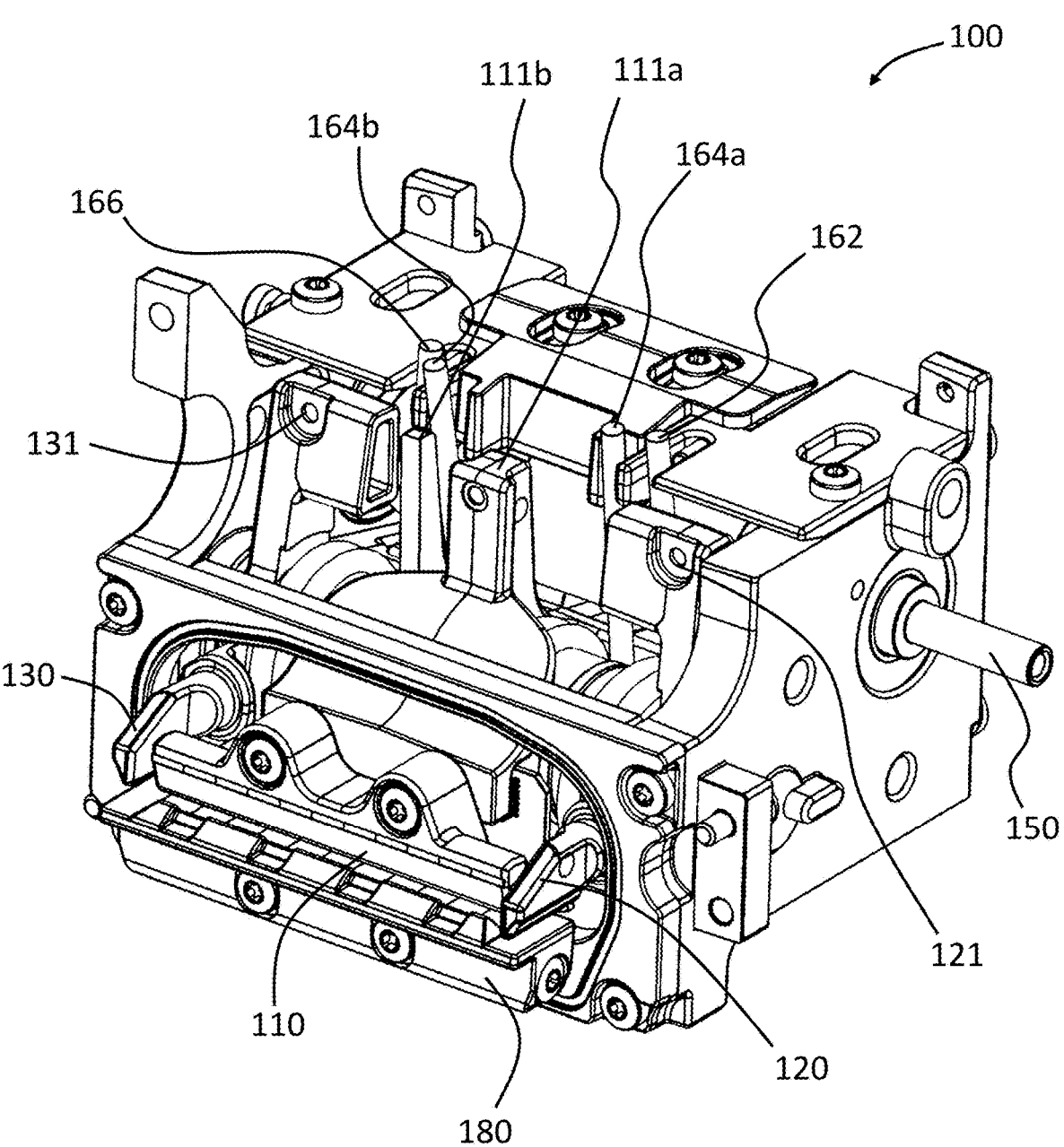
FIG. 2A is a perspective view of a peristaltic pump, in accordance with various aspects of the present disclosure.
Figure 2B:
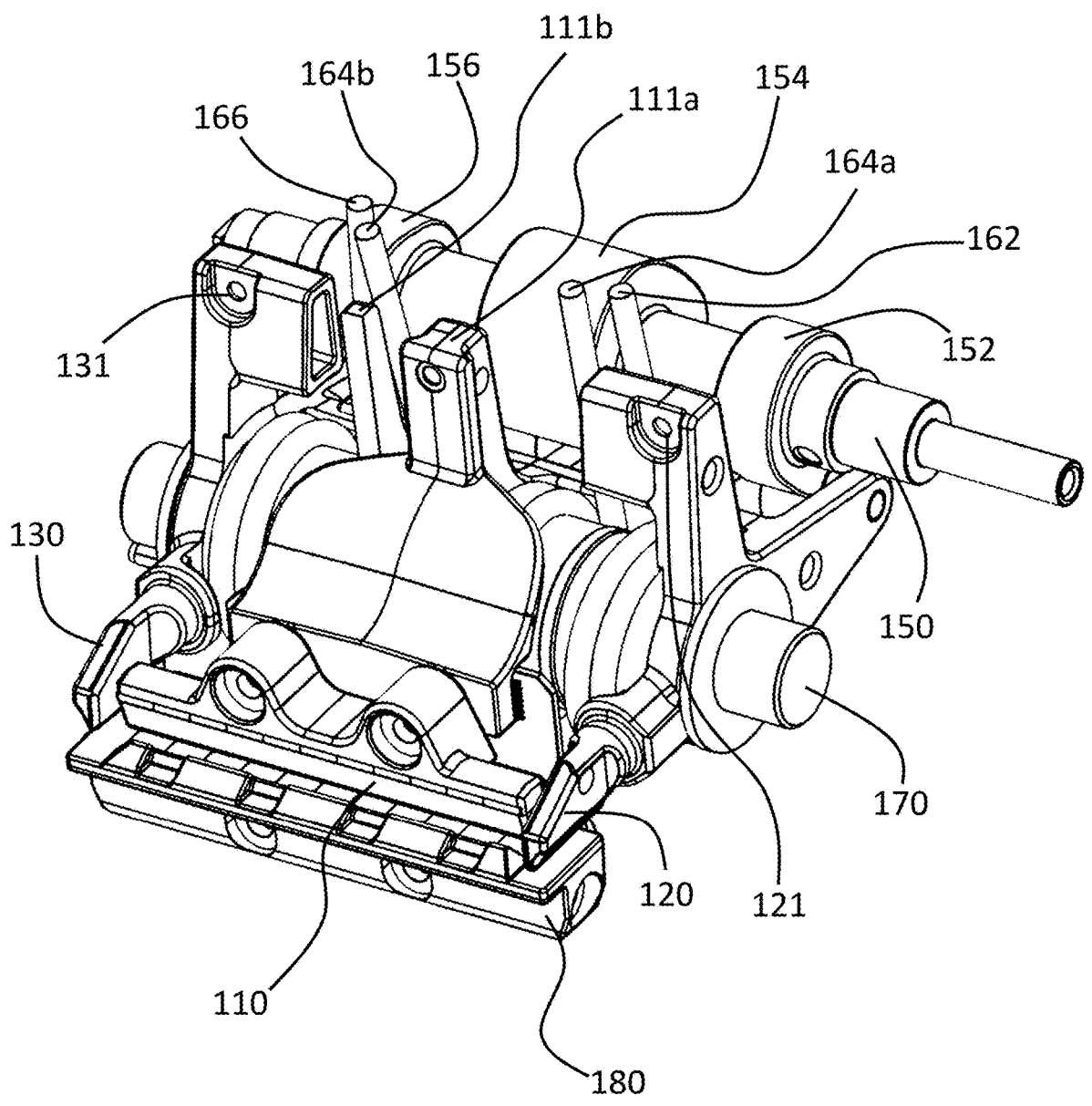
FIG. 2B is a simplified view of the peristaltic pump of FIG. 2A.

FIG. 2A is a perspective view of a peristaltic pump 100, in accordance with various aspects of the present disclosure. FIG. 2B is a simplified view of the peristaltic pump 100 of FIG. 2A. In the depicted example, the peristaltic pump 100 can peristaltically manipulate a tubing (not shown) to modulate the flow of medical fluid to the patient. In some embodiments, an upstream portion of the tubing is in fluid communication with a source of medical fluid, such as an IV bag or other medical fluid container, and the downstream portion of the tubing is in fluid communication with IV tubing to the patient. In some embodiments, the peristaltic pump 100 repeatedly cycles between a filling phase and a delivery phase to administer fluid to the patient. As described herein, the peristaltic pump 100 allows for volume measurements and air detection without requiring a dedicated measurement phase.

In the depicted example, the peristaltic pump 100 includes a plunger 110, an upstream occluder or valve 120, and a downstream occluder or valve 130, each configured to contact and manipulate the tubing to deliver fluid from a fluid source to the patient. In some embodiments, the plunger 110, the upstream valve 120, and the downstream valve 130 can move in coordinated, sequential steps to pump fluid through the tubing. The tubing can be formed from a mechanically resilient material. The tubing can be supported by a backer 180 as the plunger 110, the upstream valve 120, and/or the downstream valve 130 contact and manipulate the tubing.

As described herein, the plunger 110, the upstream valve 120, and/or the downstream valve 130 can be moved by one or more actuators. The movement of actuators that control the plunger 110, the upstream valve 120, and/or the downstream valve 130 can be coordinated, or otherwise sequenced. In the depicted example, the movement of the plunger 110, the upstream valve 120, and/or the downstream valve 130 is cyclical.

Figure 3:
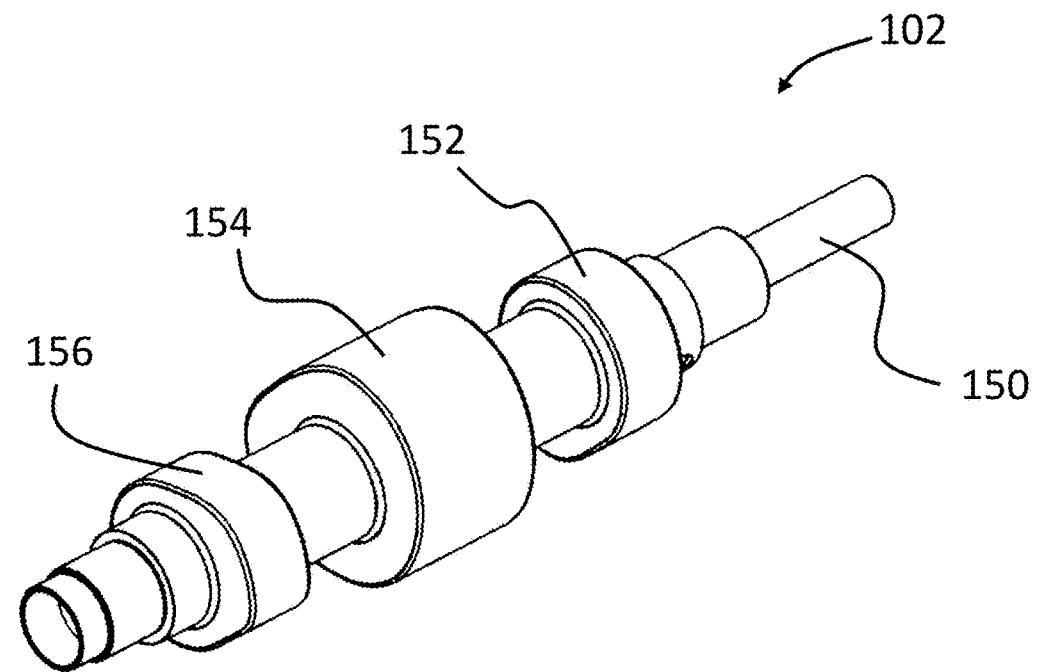
FIG. 3 is an exploded view of components of the peristaltic pump of FIG. 2A.
Figure 3:
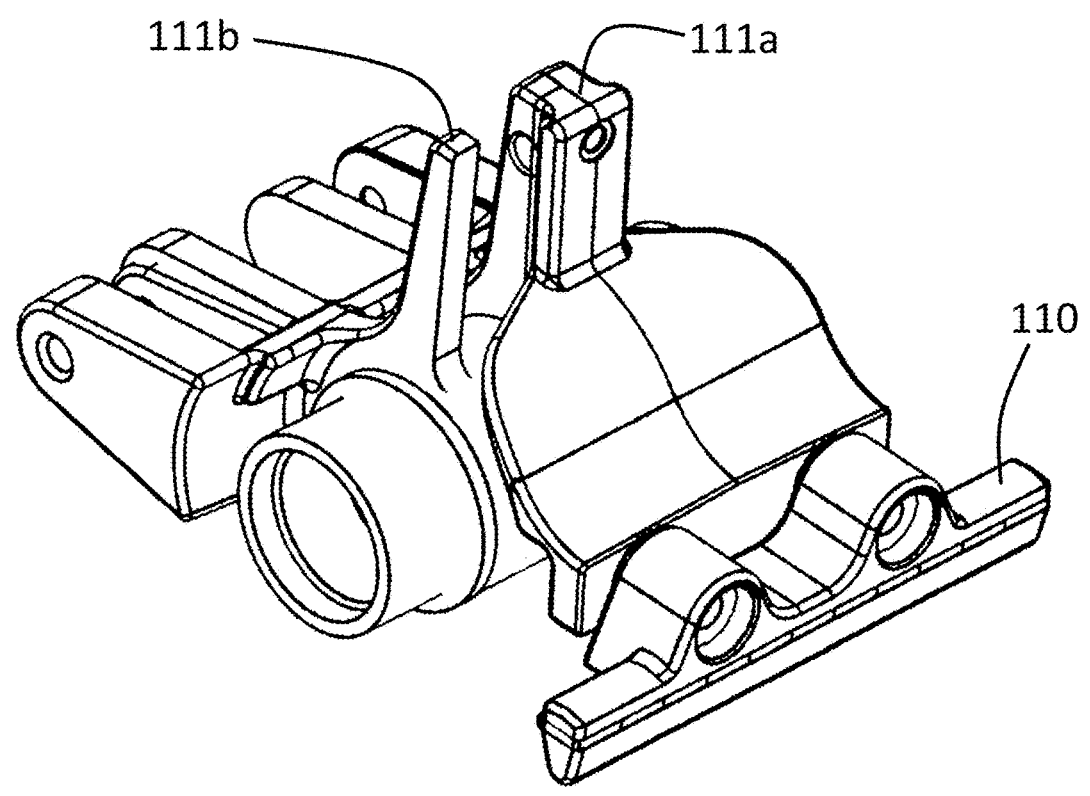

FIG. 3 is an exploded view of components of the peristaltic pump 100 of FIG. 2A. With reference to FIGS. 2A-3, the peristaltic pump 100 can include a camshaft 150 to actuate the plunger 110, the upstream valve 120, and/or the downstream valve 130. In the depicted example, the camshaft 150 includes one or more cam lobes, such as a plunger cam lobe 154, an upstream valve cam lobe 152, and/or a downstream valve cam lobe 156.

As described herein, the geometry of the respective cam lobes can be shaped or modified to allow for a desired actuation or movement of the plunger 110, the upstream valve 120, and/or the downstream valve 130. For example, portions of a cam lobe with a larger radius can allow for the plunger 110, the upstream valve 120, and/or the downstream valve 130 to open or lift further from the tubing and/or backer 180 while portions of a cam lobe with a smaller radius can allow the plunger 110, the upstream valve 120, and/or the downstream valve 130 to closer or otherwise be urged toward the tubing and/or backing.

In some embodiments, the cam lobes of the camshaft 150 actuate one or more rockers to control the plunger 110, the upstream valve 120, and/or the downstream valve 130. As can be appreciated, the geometry of the rockers described herein can be configured to provide a desired actuation ratio between the movement of the plunger 110, the upstream valve 120, and/or the downstream valve 130 and the geometry of the plunger cam lobe 154, upstream valve cam lobe 152, and/or the downstream valve cam lobe 156, respectively. As described herein, certain rockers, such as the second plunger valve rocker 111b may move independently or may otherwise not be directly actuated by the camshaft 150. The first plunger valve rocker 111*a*, the second plunger valve rocker 111*b*, the upstream valve rocker 121, and/or the downstream valve rocker 131 can each rotate or pivot about a pivot shaft 170.

In the depicted example, biasing members, such as springs can urge the plunger 110, the upstream valve 120, and/or the downstream valve 130 toward the tubing and/or the backer 180. In some embodiments, biasing members can act upon the rockers to urge the plunger 110, the upstream valve 120, and/or the downstream valve 130 toward the tubing and/or the backer 180. During operation, actuation of the plunger 110, the upstream valve 120, and/or the downstream valve 130 by the camshaft can overcome the biasing force applied by the biasing members to lift or otherwise actuate the plunger 110, the upstream valve 120, and/or the downstream valve 130.

Further, the arrangement or phasing of the cam lobes about the camshaft 150 can be modified to provide a desired sequence of actuation or movement of the plunger 110, the upstream valve 120, and/or the downstream valve 130 as the camshaft 150 is rotated. For example, the plunger cam lobe 154, the upstream valve cam lobe 152, and/or the downstream valve cam lobe 156 can each have a cam profile and/or a relative arrangement that eliminates or otherwise does not include a dedicated measurement phase where the plunger 110 is actuated against a pumping volume of the tubing closed by the upstream valve 120 and the downstream valve 130.

In the depicted example, the peristaltic pump 100 includes a split rocker arrangement with a first plunger valve rocker 111*a* directly coupled to the plunger 110 and a second plunger valve rocker 111*b* configured to act upon the first plunger valve rocker 111*a*. In some embodiments, the first plunger valve rocker 111*a* is spaced apart, decoupled, not aligned, or otherwise not directly actuated by the plunger cam lobe 154. As can be appreciated, the first plunger valve rocker 111*a* and therefore the plunger 110 may be independently moved or actuated separate from the actuation of the plunger cam lobe 154.

In the depicted example, a first plunger biasing member 164*a* can act upon the first plunger valve rocker 111*a* to urge the plunger 110 toward the tubing and/or the backer 180. As can be appreciated, the biasing force applied by the first plunger biasing member 164*a* to the first plunger valve rocker 111*a* and the plunger 110 can be a constant or chronic force that is independent of the rotation of the camshaft 150. During operation, the arrangement of the first plunger valve rocker 111*a* and the first plunger biasing member 164*a* can allow the plunger 110 to maintain contact with the tubing. As can be appreciated, the force applied by the first plunger biasing member 164*a* can be sufficient for the plunger 110 to maintain contact with the tubing without damaging the tubing.

In the depicted example, the position of the plunger 110 can be used to determine the volume of fluid administered by the peristaltic pump 100. During operation, the height of the plunger 110 can be used to determine the height of the pumping volume within the tubing, which can be used to determine the volume of fluid administered by the peristaltic pump 100. Advantageously, the arrangement of the first plunger biasing member 164*a* and the first plunger valve rocker 111*a* allows for the plunger 110 to permit volume measurements without exerting excess force or requiring a dedicated measurement phase.

In the depicted example, the second plunger valve rocker 111*b* is aligned, positioned, or otherwise configured to be actuated by the plunger cam lobe 154. During operation, a portion of the second plunger valve rocker 111*b* can engage or slide along the cam profile of the plunger cam lobe 154 to translate the geometry of the cam profile into movement of the second plunger valve rocker 111*b*. In some embodiments, during certain movements (e.g., during a delivery phase of operation) the second plunger valve rocker 111*b* can engage with the first plunger valve rocker 111*a* to move the plunger 110 relative to the tubing in response to actuation from the plunger cam lobe 154.

In the depicted example, a second plunger biasing member 164*b* can act upon the second plunger valve rocker 111*b* to urge the second plunger valve rocker 111*b* toward the first plunger valve rocker 111*a*. During certain portions of operation (e.g., the delivery phase of operation) the second plunger biasing member 164*b* can force the second plunger valve rocker 111*b* to engage with the first plunger valve rocker 111*a* and urge the plunger 110 toward the tubing and/or the backer 180. As can be appreciated, actuation of the second plunger valve rocker 111*b* by the rotation of the plunger cam lobe 154 can overcome the biasing force to disengage the second plunger valve rocker 111*b* from the first plunger valve rocker 111*a*. Accordingly, the biasing force applied by the second plunger biasing member 164*b* to the first plunger valve rocker 111*a* and/or the plunger 110 can vary in response to the actuation of the second plunger valve rocker 111*b* by the rotation of the plunger cam lobe 154. During operation, the arrangement of the second plunger valve rocker 111*b* and the second plunger biasing member 164*b* relative to the first plunger valve rocker 111*a* and the first plunger biasing member 164*a* allows the peristaltic pump 100 to apply additional force to the plunger during certain portions of operation (e.g., the delivery phase) while allowing the first plunger biasing member 164*a* to maintain a chronic biasing force against the tubing. In some embodiments, the force applied by the second plunger biasing member 164*b* is higher than the biasing force applied by the first plunger biasing member 164*a*. Optionally, the force applied by the second plunger biasing member 164*b* is sufficient to allow fluid delivery. In some embodiments, the first plunger biasing member 164*a* and the second plunger biasing member 164*b* cooperatively provide sufficient force to allow for fluid delivery.

In some embodiments, an upstream valve rocker 121 is coupled to the upstream valve 120 and can move the upstream valve 120 in response to actuation from the upstream valve cam lobe 152. During operation, a portion of the upstream valve rocker 121 can engage or slide along the cam profile of the upstream valve cam lobe 152 to translate the geometry of the cam profile into movement of the upstream valve 120 relative to the tubing.

As illustrated, an upstream valve biasing member 162 can act upon the upstream valve rocker 121 to urge the upstream valve 120 toward the tubing and/or the backer 180. As can be appreciated, actuation of the upstream valve rocker 121 by the rotation of the upstream valve cam lobe 152 can overcome the biasing force to lift or otherwise actuate the upstream valve 120.

Similarly, a downstream valve rocker 131 is coupled to the downstream valve 130 and can move the downstream valve 130 in response to actuation from the downstream valve cam lobe 156. During operation, a portion of the downstream valve rocker 131 can engage or slide along the cam profile of the downstream valve cam lobe 156 to translate the geometry of the cam profile into movement of the downstream valve 130 relative to the tubing.

Similarly, a downstream valve biasing member 166 can act upon the downstream valve rocker 131 to urge the downstream valve 130 toward the tubing and/or the backer 180. As can be appreciated, actuation of the downstream valve rocker 131 by the rotation of the downstream valve cam lobe 156 can overcome the biasing force to lift or otherwise actuate the downstream valve 130.

FIG. 4A is an illustration of the peristaltic pump 100 of FIG. 2A in a filling phase, in accordance with various aspects of the present disclosure. During operation, the tubing 102 draws in medical fluid 10 during the filling phase. As illustrated, the plunger 110 is withdrawn or retracted from a compressed portion of the tubing 102, allowing the tubing walls 104 to resiliently expand the pumping volume 107 to an original or expanded state.

In the depicted example, the expansion of the pumping volume 107 draws in fluid into the pumping volume 107. The mechanical resilience of the tubing 102 allows the tubing walls 104 to expand from a compressed state to an expanded state, expanding the pumping volume 107. The rate at which the pumping volume 107 rebounds from a compressed state to an expanded state can determine the amount of fluid that can be drawn into the pumping volume 107 in a given period of time.

As illustrated, during the expansion of the pumping volume 107, the downstream portion 108 of the tubing 102 is blocked, pinched, or otherwise occluded by the downstream valve 130 to prevent or restrict backflow or contamination of fluid into the pumping volume 107.

In the depicted example, the downstream valve 130 is actuated, moved downward, or otherwise engaged to compress the tubing walls 104 of the tubing 102 at the downstream portion 108 to occlude flow through the downstream portion 108 of the tubing 102. The downstream valve 130 can include a beveled engagement portion to contact the tubing 102. When engaged, the downstream valve 130 can prevent or restrict flow or fluid communication from the downstream portion 108 into the pumping volume 107.

During the expansion of the pumping volume 107, medical fluid 10 is drawn into pumping volume 107 from the upstream portion 106 of the tubing 102. As illustrated, during the expansion of the pumping volume 107, the upstream portion 106 of the tubing 102 is unobstructed by the upstream valve 120, permitting medical fluid 10 into the pumping volume 107. During operation, the upstream valve 120 is withdrawn or retracted from a compressed portion of the tubing 102, allowing the tubing walls 104 to resiliently expand the upstream portion 106 to an original or expanded state.

In the depicted example, the expansion of the upstream portion 106 permits the flow of medical fluid 10 into the pumping volume 107. The mechanical resilience of the tubing 102 allows the tubing walls 104 to expand from a compressed state to an expanded state, expanding the cross-sectional profile or flow area of the upstream portion 106. The amount of medical fluid 10 drawn into the pumping volume 107 during the filling phase can be determined by the timing and sequence of the plunger 110, the upstream valve 120, a viscosity of the medical fluid 10, and the mechanical properties of the tubing 102.

Advantageously, and as described herein, the first plunger biasing member 164a can maintain a constant or chronic force to allow the plunger 110 to maintain contact with the tubing 102 during the filling phase to permit measurement of the pumping volume. In the depicted example, the force applied by the first plunger biasing member 164a can be sufficient to maintain contact with the tubing 102 while allowing for the pumping volume 107 to be filled.

FIG. 4B is an illustration of the peristaltic pump 100 of FIG. 2A in a delivery phase, in accordance with various aspects of the present disclosure. FIG. 4C is an illustration of the peristaltic pump 100 of FIG. 2A in a delivered position, in accordance with various aspects of the present disclosure. With reference to FIGS. 4B and 4C, the peristaltic pump 100 delivers medical fluid through a downstream portion 108 to a downstream location, such as a patient. As illustrated, the plunger 110 is actuated, moved downward, or otherwise engaged to compress the tubing walls 104 of the tubing 102 to compress the pumping volume 107 to a compressed or reduced state.

During operation, the compression of the pumping volume 107 expels or otherwise administers fluid from the pumping volume 107 to a downstream location. The rate of administration of the medical fluid can be controlled by the force and velocity of the plunger 110.

As described herein, the first plunger biasing member 164a and the second plunger biasing member 164b cooperatively force the plunger 110 to compress the pumping volume 107 to a compressed or reduced state. In some embodiments, the second plunger biasing member 164b can force the plunger 110 to compress the pumping volume 107 to a compressed or reduced state without the cooperation of the first plunger biasing member 164a.

During administration, the upstream portion 106 of the tubing 102 is blocked, pinched, or otherwise occluded by the upstream valve 120 to prevent or restrict inadvertent fluid flow into the pumping volume 107 and to prevent or restrict backflow of fluid into the medical container from the pumping volume 107.

In the depicted example, the upstream valve 120 is actuated, moved downward, or otherwise engaged to compress the tubing walls 104 of the tubing 102 at the upstream portion 106 to occlude flow through the upstream portion 106 of the tubing 102. The upstream valve 120 can include a beveled engagement portion to contact the tubing 102. When engaged, the upstream valve 120 can prevent or restrict flow or fluid communication between the upstream portion 106 and the pumping volume 107.

During the compression of the pumping volume 107, medical fluid is forced from the pumping volume 107 to a downstream location through the downstream portion 108 of the tubing 102. As illustrated, during the compression of the pumping volume 107, the downstream portion 108 of the tubing 102 is unobstructed by the downstream valve 130, permitting medical fluid 10 to flow out of the tubing 102. During operation, the downstream valve 130 is withdrawn or retracted from a compressed portion of the tubing 102, allowing the tubing walls 104 to resiliently expand the downstream portion 108 to an original or expanded state.

In the depicted example, the expansion of the downstream portion 108 permits the flow of medical fluid 10 out of the pumping volume 107. The mechanical resilience of the tubing 102 allows the tubing walls 104 to expand from a compressed state to an expanded state, expanding the cross-sectional profile or flow area of the downstream portion 108. The rate at which the downstream portion 108 rebounds from a compressed state to an expanded state can limit the size of the flow area or opening out of the pumping volume 107. Therefore, the rate at which the downstream portion 108 rebounds from a compressed state to an expanded state can limit or restrict the amount of fluid that can flow out of the pumping volume 107 in a given period of time.

The amount of medical fluid 10 administered from the pumping volume 107 during the delivery phase can be determined by the timing and sequence of the plunger 110, the downstream valve 130 and the mechanical properties of the tubing 102.

During operation, the arrangement of the first plunger valve rocker 111a, the first plunger cam lobe 154a, and the first plunger biasing member 164a can allow the plunger 110 to contact the tubing during a measurement phase without administering the fluid within the pumping volume or damaging the tubing. In some embodiments, the first plunger valve rocker 111a, the first plunger cam lobe 154a, and the first plunger biasing member 164a may allow the plunger 110 to contact the tubing at all times. The first plunger biasing member 164a may apply a force to the plunger 110 to allow the plunger 110 to contact the tubing 102 to determine the height of the tubing 102, the pumping volume 107 and/or the presence of air. In the depicted example, the force applied by the first plunger biasing member 164a can be sufficient to maintain contact with the tubing 102 without creating excess pressure within the pumping volume.

During operation, the tubing 102 (shown in FIG. 1) draws in a medical fluid 10 during the filling phase. The plunger 110 is withdrawn or retracted from a compressed portion of the tubing 102, allowing the tubing walls 104 to resiliently expand the pumping volume 107 to an original or expanded state. The mechanical resilience of the tubing 102 allows the tubing walls 104 to expand from a compressed state to an expanded state, expanding the pumping volume 107. The rate at which the pumping volume 107 rebounds from a compressed state to an expanded state can determine the amount of fluid that can be drawn into the pumping volume 107 in a given period of time.

During the expansion of the pumping volume 107, the downstream portion 108 of the tubing 102 may be blocked, pinched, or otherwise occluded by the downstream valve 130 to prevent or restrict backflow, air or contamination of fluid into the pumping volume 107. The downstream valve 130 may be actuated, moved downward, or otherwise engaged to compress the tubing walls 104 of the tubing 102 at the downstream portion 108 to occlude flow through the downstream portion 108 of the tubing 102. The downstream valve 130 can include a beveled engagement portion to contact the tubing 102. When engaged, the downstream valve 130 can prevent or restrict flow or fluid communication from the downstream portion 108 into the pumping volume 107.

During the expansion of the pumping volume 107, medical fluid 10 is drawn into the pumping volume 107 from the upstream portion 106 of the tubing 102. As illustrated, during the expansion of the pumping volume 107, the upstream portion 106 of the tubing 102 is unobstructed by the upstream valve 120, permitting medical fluid 10 into the pumping volume 107. During operation, the upstream valve 120 is withdrawn or retracted from a compressed portion of the tubing 102, allowing the tubing walls 104 to resiliently expand the upstream portion 106 to an original or expanded state.

The expansion of the upstream portion 106 may permit the flow of medical fluid 10 into the pumping volume 107. The mechanical resilience of the tubing 102 allows the tubing walls 104 to expand from a compressed state to an expanded state, expanding the cross-sectional profile or flow area of the upstream portion 106. The amount of medical fluid 10 drawn into the pumping volume 107 during the filling phase can be determined by the timing and sequence of the plunger 110, the upstream valve 120, a viscosity of the medical fluid 10, and the mechanical properties of the tubing 102. Advantageously, and as described herein, the first plunger biasing member 164a can maintain a constant or chronic force to allow the plunger 110 to maintain contact with the tubing 102 during the filling phase to permit measurement of the pumping volume. In the depicted example, the force applied by the first plunger biasing member 164a can be sufficient to maintain contact with the tubing 102 while allowing for the pumping volume 107 to be filled.

Figure 4:
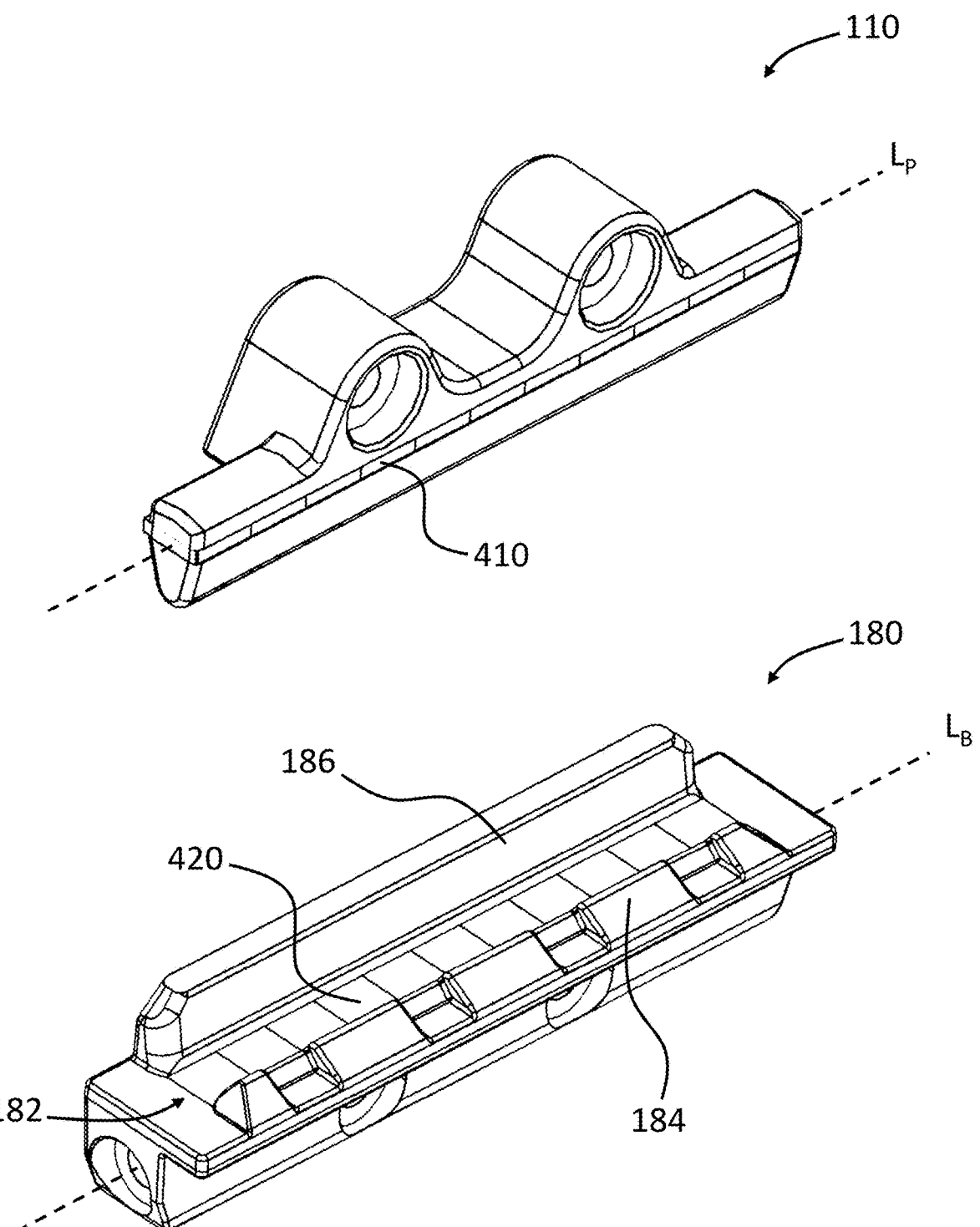
FIG. 4 is an exploded view of a plunger and a backer of the peristaltic pump of FIG. 2A.

FIG. 4 is an exploded view of the plunger 110 and the backer 180. As shown, the plunger 110 may include a plunger air detection module 410 and the backer 180 may include a backer air detection module 420. The air detection modules 410, 420 may extend a length of the plunger 110 and backer 180 along a longitudinal axis $L_P$, $P_B$ thereof, respectively. Air detection modules 410, 420 may span a partial length of the plunger 110 and backer 180, respectively. Air detection modules 410, 420 may include a plurality of elements, each element taking air in line measurements. In one embodiment, the air detection modules 410, 420 may include a single element. The air detection module 410 may be transmit a signal and the air detection module 420 may be receive the signal. In one embodiment, the air detection module 420 may be transmit a signal and the air detection module 410 may be receive the signal. The air detection modules 410, 420 may be generally parallel to each other when the plunger 110 is proximate the backer 180, particularly in the engaged position during a measurement.

The air detection module 410, 420 may be a piezoelectric (piezo) array. As shown in FIG. 4, the plunger 110 may include a slot or cutout shaped and sized to receive the air detection module 410. The backer 180 may include a slot or cutout shaped and sized to receive the air detection module 410. The piezo array may include one or more element making up the air detection module 410, 420. Each element of the piezo array may be a square. In one embodiment, each element of the piezo array may be rectangular or another polygonal shape. In one embodiment, each element of the piezo array may be circular. To prevent the tubing segment from moving relative to the pump 100, a channel 182 may be defined around the slot or cutout of the backer 180. The channel 182 may include a front wedge 184 and a rear barrier 186 extending from the backer 180. The front wedge 184 may be angled so as to force the tubing segment toward the rear barrier 186 when the tubing segment is disposed therein. There may be a plurality of front wedges 184 extend substantially along the length of the backer 180 along the longitudinal axis $L_B$. The rear barrier 186 may be a generally flat feature extending from the backer 180. The rear barrier 186 may extend substantially along the length of the backer 180 along the longitudinal axis $L_B$.

Each element in the piezo array may be approximately 4 mm wide by 4 mm. Each element in the piezo array may be approximately 2 mm wide by 2 mm. Each element in the piezo array may be approximately 2.5 mm wide by 2.5 mm. Each element in the piezo array may be approximately 3 mm wide by 3 mm. Each element in the piezo array may be approximately 3.5 mm wide by 3.5 mm. Each element in the piezo array may be approximately 4.5 mm wide by 4.5 mm. Each element in the piezo array may be approximately 5 mm wide by 5 mm. Each element in the piezo array may be approximately 5.5 mm wide by 5.5 mm. Each element in the piezo array may be approximately 6 mm wide by 6 mm.

Each element in the piezo array may be approximately 0.86 mm thick. Each element in the piezo array may be approximately 0.8 mm thick. Each element in the piezo array may be approximately 0.81 mm thick. Each element in the piezo array may be approximately 0.82 mm thick. Each element in the piezo array may be approximately 0.83 mm thick. Each element in the piezo array may be approximately 0.84 mm thick. Each element in the piezo array may be approximately 0.85 mm thick. Each element in the piezo array may be approximately 0.87 mm thick. Each element in the piezo array may be approximately 0.88 mm thick. Each element in the piezo array may be approximately 0.89 mm thick. Each element in the piezo array may be approximately 0.9 mm thick. Each element in the piezo array may be approximately 0.91 mm thick.

Figure 5:
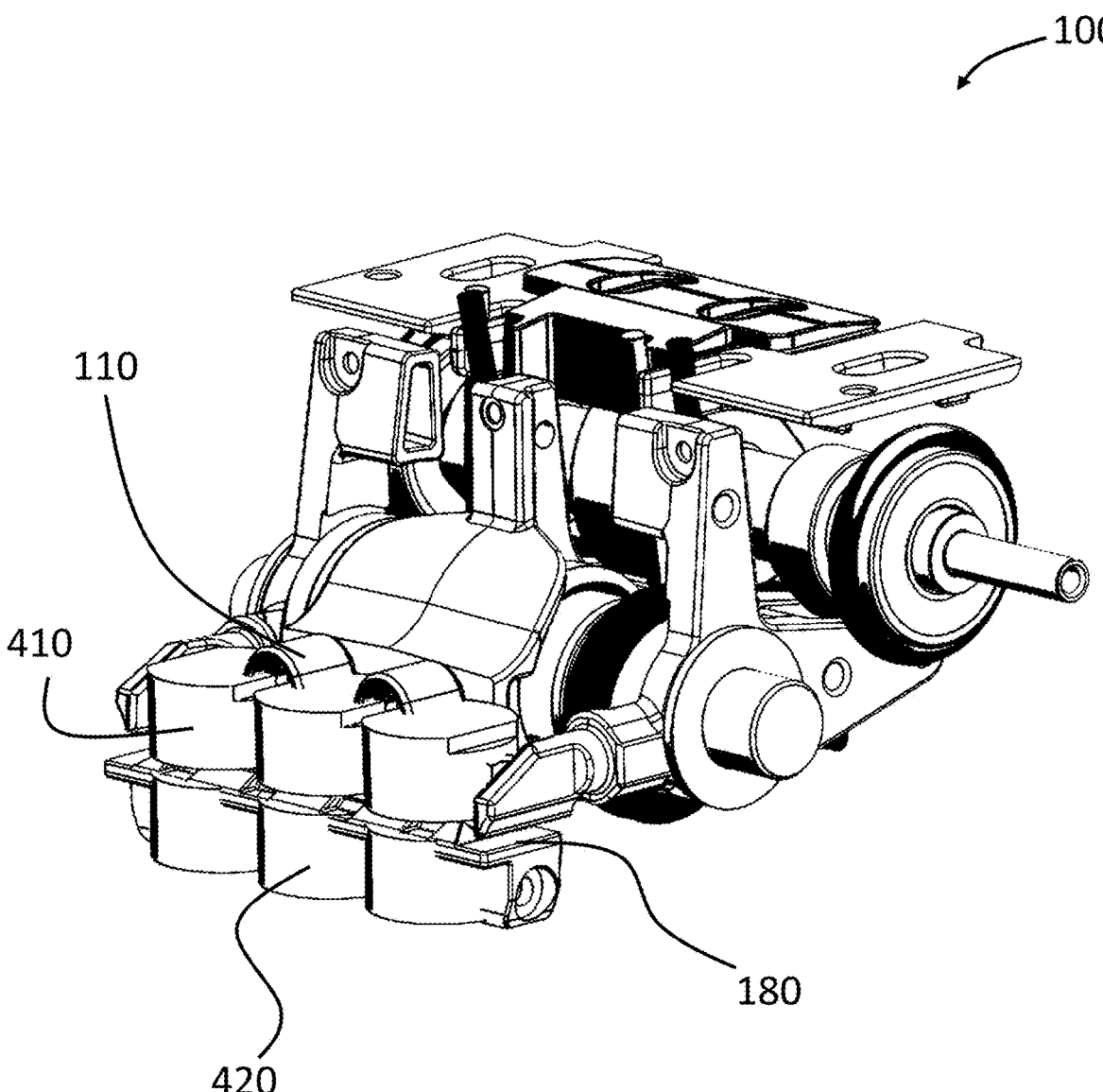
FIG. 5 is a perspective view of a peristaltic pump, in accordance with various aspects of the present disclosure.

FIG. 5 illustrates an embodiment of air detection modules 410, 420 coupled to the plunger 110 and backer 180, respectively. In this example, air detection module 410 may be a transmitter and air detection module 420 may be a receiver. In one embodiment, air detection module 420 may be a transmitter and air detection module 410 may be a receiver. There may be a housing (not shown) covering the air detection modules 410, 420 to protect them from outside forces and debris. There may be three air detection modules 410, 420 disposed on the plunger 110 and the backer 180, respectively. In one embodiment, there may be one air detection module 410, 420 disposed on the plunger 110 and the backer 180, respectively. The air detection module 410, 420 may be cylindrical in shape. The air detection module 410, 420 may include the same element as makes up the piezo array shown in FIG. 4.

The rate of administration of the medical fluid can be controlled by the force and velocity of the plunger 110. Upon detection of air in the tubing, the rate of fluid volume traveling through the pump may be controlled to ensure a save infusion of the fluid to the patient.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A pump for detecting air comprising:
a plunger movable to selectively engage a tubing segment comprising a fluid;
a backer configured to support the tubing segment when the plunger engages the tubing segment;
a plunger air detection module extending within the plunger and configured to transmit a signal;
a backer air detection module within the backer and configured to receive the signal from the plunger air detection module;
a camshaft configured to move the plunger between an engaged position in contact with the tubing segment and a disengaged position spaced apart from the tubing segment; and
a first biasing member configured to urge the plunger toward the tubing segment to maintain contact with the tubing segment in the engaged position, wherein the plunger is urged toward the tubing segment and the backer.

2. The pump of claim 1, further comprising:
the backer configured to engage the tubing segment in the engaged position and the disengaged position.

3. The pump of claim 2, wherein the backer comprises a channel configured to prevent movement of the tubing segment relative to the pump.

4. The pump of claim 3, wherein the channel extends a longitudinal length of the backer.

5. The pump of claim 4, wherein the channel is defined by a front wedge and a rear barrier extending therefrom along a longitudinal length of the backer.

6. The pump of claim 2, wherein the backer comprises a cutout extending along a longitudinal length thereof.

7. The pump of claim 6, wherein the cutout is configured to receive the backer air detection module.

8. The pump of claim 7, wherein the backer air detection module is parallel to the plunger air detection module.

9. The pump of claim 1, wherein the backer air detection module is configured to receive the signal when the plunger is in the engaged position.

10. The pump of claim 1, wherein the plunger air detection module comprises a plurality of elements.

11. The pump of claim 10, wherein the plunger air detection module comprises a piezoelectric array of elements.

12. The pump of claim 1, further comprising a slot defined in the plunger.

13. The pump of claim 12, wherein the plunger air detection module is disposed in the slot.

14. The pump of claim 1, wherein the plunger does not deform the tubing segment in the engaged position.

15. A method comprising:
providing a tubing segment within a pump, the tubing segment comprising a fluid traveling therethrough;
urging a plunger toward the tubing segment and a backer such that the plunger is configured to maintain contact with the tubing segment as the fluid travels therethrough, and the backer is configured to support the tubing segment; and
emitting a signal from a plunger air detection module extending within the plunger through the tubing segment, and receiving the signal by a backer air detection module of the backer.

16. The method of claim 15, further comprising the backer air detection module receiving the signal when the plunger is in an engaged position in contact with the tubing segment.

17. The method of claim 15, further comprising:
moving the plunger with a camshaft to increase or decrease a cross section of the tubing segment to modulate a rate of flow of the fluid through the tubing segment.

18. The method of claim 15, further comprising:
moving the plunger with a camshaft to reduce a cross section of the tubing segment to prevent a flow of fluid through the tubing segment.

19. The method of claim 15, wherein the backer air detection module is parallel to the plunger air detection module when the plunger is urged toward the tubing segment to maintain contact with the tubing segment.

20. The method of claim 15, wherein the plunger does not deform the tubing segment when the plunger is urged toward the tubing segment to maintain contact with the tubing segment.

* * * * *